US006889567B2

(12) United States Patent
Cabuz

(10) Patent No.: US 6,889,567 B2
(45) Date of Patent: May 10, 2005

(54) 3D ARRAY INTEGRATED CELLS FOR THE SAMPLING AND DETECTION OF AIR BOUND CHEMICAL AND BIOLOGICAL SPECIES

(75) Inventor: Cleopatra Cabuz, Edina, MN (US)

(73) Assignee: Honeywell International Inc., Morristown, NJ (US)

( * ) Notice: Subject to any disclaimer, the term of this patent is extended or adjusted under 35 U.S.C. 154(b) by 0 days.

(21) Appl. No.: 10/340,231

(22) Filed: Jan. 10, 2003

(65) Prior Publication Data

US 2004/0020265 A1 Feb. 5, 2004

Related U.S. Application Data

(62) Division of application No. 09/586,093, filed on Jun. 2, 2000, now Pat. No. 6,568,286.

(51) Int. Cl.[7] .............................. G01N 1/26; G01N 1/20; G01N 1/14
(52) U.S. Cl. ................................ 73/863.23; 73/863.11; 417/413.3; 417/413.1
(58) Field of Search ................................. 417/413, 322, 417/413.1, 413.2, 413.3; 73/863.23, 863.11

(56) References Cited

U.S. PATENT DOCUMENTS

| | | | |
|---|---|---|---|
| 2,403,692 A | 7/1946 | Tibbetts | |
| 2,975,307 A | 3/1961 | Shroeder et al. | |

(Continued)

FOREIGN PATENT DOCUMENTS

| | | |
|---|---|---|
| DE | 19617852 | 10/1997 |
| EP | 0744821 A | 11/1996 |
| JP | 5-219760 | 8/1993 |
| SU | 744877 | 6/1980 |

OTHER PUBLICATIONS

Cabutz, "Tradeoffs in MEMS Materials". SPIE vol. 2881, pp. 160–170 (Oct. 1996).

C. Cabuz et al., "High Reliability Touch–Mode Electrostatic Actuators", Technical Digest of the Solid State Sensor and Actuator Workshop, Hilton Head, S.C., Jun. 8–11, 1998, pp. 296–299.

(Continued)

Primary Examiner—Hezron WIlliams
Assistant Examiner—Rose M. Miller
(74) Attorney, Agent, or Firm—Kris T. Fredrick

(57) ABSTRACT

An integrated mesopump-sensor suitable for disposition in two- and three-dimensional arrays having small dimensions is disclosed. One mesopump is formed of an electrostatically attractable flexible diaphragm disposed through cavities or pumping chambers formed between two opposing electrostatically chargeable material layers. Fluid is pumped through the chambers by sequentially moving the diaphragm toward the first chargeable layer, then towards the second chargeable layer, which can pull and push the fluid through a series of chambers, and past the sensor. One group of sensors utilizes multiple and varied chemoresistive sensors which can vary in resistance differently in response to the presence of various analytes. Another group of sensors utilizes chemo-fluorescent sensors that fluoresce in the presence of particular analytes. Some mesopump-sensor systems can be manufactured using MEMS technology and can be coupled to controllers for sequencing the pumps and analyzing sensor outputs using methods including Principle Component Analysis.

17 Claims, 10 Drawing Sheets

U.S. PATENT DOCUMENTS

| | | |
|---|---|---|
| 3,304,446 A | 2/1967 | Martinek et al. |
| 3,381,623 A | 5/1968 | Elliot |
| 3,641,373 A | 2/1972 | Elkuch |
| 3,769,531 A | 10/1973 | Elkuch |
| 3,803,424 A | 4/1974 | Smiley et al. |
| 3,947,644 A | 3/1976 | Uchikawa |
| 4,115,036 A | 9/1978 | Paterson |
| 4,140,936 A | 2/1979 | Bullock |
| 4,197,737 A | 4/1980 | Pittman |
| 4,453,169 A | 6/1984 | Martner |
| 4,478,076 A | 10/1984 | Bohrer |
| 4,478,077 A | 10/1984 | Bohrer |
| 4,498,850 A | 2/1985 | Perlov et al. |
| 4,501,144 A | 2/1985 | Higashi et al. |
| 4,539,575 A | 9/1985 | Nilsson |
| 4,576,050 A | 3/1986 | Lambert |
| 4,651,564 A | 3/1987 | Johnson et al. |
| 4,654,546 A | 3/1987 | Kirjavainen |
| 4,756,508 A | 7/1988 | Giachino et al. |
| 4,759,210 A * | 7/1988 | Wohltjen ................. 417/413.3 |
| 4,786,472 A | 11/1988 | McConnell et al. |
| 4,821,999 A | 4/1989 | Ohtaka |
| 4,911,616 A | 3/1990 | Laumann, Jr. |
| 4,938,742 A | 7/1990 | Smits |
| 4,939,405 A | 7/1990 | Okuyama et al. |
| 5,065,978 A | 11/1991 | Albarda et al. |
| 5,069,419 A | 12/1991 | Jerman |
| 5,078,581 A * | 1/1992 | Blum et al. ................. 417/322 |
| 5,082,242 A | 1/1992 | Bonne et al. |
| 5,085,562 A | 2/1992 | van Lintel |
| 5,096,388 A | 3/1992 | Weinberg |
| 5,129,794 A | 7/1992 | Beatty |
| 5,148,074 A | 9/1992 | Fujita et al. |
| 5,171,132 A | 12/1992 | Miyazaki et al. |
| 5,176,358 A | 1/1993 | Bonne |
| 5,180,288 A | 1/1993 | Richter et al. |
| 5,180,623 A | 1/1993 | Ohnstein |
| 5,192,197 A | 3/1993 | Culp |
| 5,206,557 A | 4/1993 | Bobbio |
| 5,219,278 A | 6/1993 | van Lintel |
| 5,224,843 A | 7/1993 | van Lintel |
| 5,244,537 A | 9/1993 | Ohnstein |
| 5,322,258 A | 6/1994 | Bosch et al. |
| 5,323,999 A | 6/1994 | Bonne et al. |
| 5,441,597 A | 8/1995 | Bonne et al. |
| 5,452,878 A | 9/1995 | Gravesen et al. |
| 5,499,909 A | 3/1996 | Yamada et al. |
| 5,541,465 A | 7/1996 | Higuchi et al. |
| 5,552,654 A | 9/1996 | Konno et al. |
| 5,571,401 A | 11/1996 | Lewis et al. |
| 5,642,015 A | 6/1997 | Whitehead et al. |
| 5,683,159 A | 11/1997 | Johnson |
| 5,725,363 A | 3/1998 | Bustgens et al. |
| 5,759,014 A | 6/1998 | Van Lintel |
| 5,759,015 A | 6/1998 | Van Lintel et al. |
| 5,836,750 A * | 11/1998 | Cabuz ........................ 417/322 |
| 5,863,708 A | 1/1999 | Zanzucchi et al. |
| 5,901,939 A | 5/1999 | Cabuz et al. |
| 5,911,872 A | 6/1999 | Lewis et al. |
| 6,106,245 A | 8/2000 | Cabuz |
| 6,179,586 B1 | 1/2001 | Herb et al. |
| 6,184,607 B1 | 2/2001 | Cabuz et al. |
| 6,184,697 B1 | 2/2001 | Suga |
| 6,215,221 B1 | 4/2001 | Cabuz et al. |
| 6,432,721 B1 * | 8/2002 | Zook et al. ................. 436/181 |
| 6,568,286 B1 * | 5/2003 | Cabuz ..................... 73/863.33 |
| 6,649,416 B1 * | 11/2003 | Kauer et al. ................ 436/164 |

OTHER PUBLICATIONS

Bertz, Schubert, Werner, "Silicon Grooves with Sidewall Angles to 1° made by Dry Etching".

Bustagens, Bacher, Menz, Schomburg, "Micropump Manufactured by Thermoplastic Molding" MEMS 1994.

Wagner, Quenzer, Hoerschelmann, Lisec, Juerss, "Bistable Microvalve with Pneumatically Coupled Membranes," 0-7803-2985-Jun. 1996 IEEE (1996).

Branebjerg, Gravensen A new Electrostatic Actuator Providing Improved Stroke Length and Force,: Micro Electro Mechanical Systems (Feb. 407, 1992).

Minami K et al., Fabrication of Distributed Electrostatical System, US IEEE, Inc., New York, vol. 2, No. 3, Sep. 1, 1993, pp. 121–XP000426532, ISSN: 1057–7157.

Large–Scale Linearization Circuit For Electrostatic Motors.: IBM Technical Disclosure Bulletin, US, IBM Corp. New York, vol. 37, No. 0, Oct. 1, 1994 pp. 563–564, XP000475777, ISN: 0018–8689.

Shikida, Sato, Harada, "Fabrication of an S–Shaped Microactuator," Journal of Microelectromechanical Systems, vol. 6, No. 1 (Mar. 1997).

Shikida, Sato, Characteristics of an Electrostatically–Driven Gas Valve under Hight Pressure Conditions.

Shikida, Sato, Tanaka, Kawamura, Fujisaki, Electrostatically–Actuated Gas Valve with large Conductance, 7th Intl. Conf. On Solid–State Sensors and Actuators, J. Microelectromech, Syst. vol. 3, No. 2, (Jun. 1994).

E. Halg. "On a Nonvolatile Memory Cell Based on Micro–Electro–Mechanics," Proceedings of MEMs CH2832–4/90/0000–0172 IEEE (1990).

Srinivasan et al. Self–Assembled fluorocarbon Films for Enhanced Stiction Reduction.

Jye–Shane Yang et al., "Fluorescent Porous Polymer Films as TNT Chemosensors: Electronic and Structural Effects", *J. Am. Chem. Soc.*, 1998, 120, pp. 11864–73.

Jye–Shane Yang et al., "Porous Shape Persistent Fluorescent Polymer Films: An Approach to TNT Sensory Materials", *J. Am. Chem. Soc.*, 1998, 120, pp. 5321–2.

Michael S. Freud et al., "A Chemically Diverse Conducting Polymer–Based 'Electronic Nose'", *Proceedings of the National Academy of Sciences of the United States of America*, vol. 92, No. 7, Mar. 28, 1995, pp. 2652–6.

Porex: Technologies, brochure, dated prior to Jun. 2, 2000, 4 pages.

* cited by examiner

3D ARRAY INTEGRATED CELLS FOR THE SAMPLING AND DETECTION OF AIR BOUND CHEMICAL AND BIOLOGICAL SPECIES

This application is a divisional of U.S. patent application Ser. No. 09/586,093, filed Jun. 2, 2000, now U.S. Pat. No. 6,568,286 entitled. "3D ARRAY OF INTEGRATED CELLS FOR THE SAMPLING AND DETECTION OF AIR BOUND CHEMICAL AND BIOLOGICAL SPECIES. This application is also related to U.S. Divisional Patent application Ser. No. 10/340,231, filed Jan. 10, 2003.

FIELD OF THE INVENTION

The present invention is related generally to electronic sensors for detecting airborne chemical and biological agents. More specifically, the present invention is related to microelectromechanical systems (MEMS) which can detect harmful chemical and biological agents.

BACKGROUND OF THE INVENTION

Air or gas phase sensing and measurement systems are currently used in many applications, such as industrial process controls, environmental compliance measuring, and explosive detection. In one example, on-line gas chromatography and on-line optical spectroscopy are used to measure process conditions using the gas phase components. In another example, the concentration of combustion gases and stack particulates are measured to insure environmental regulatory compliance. Such systems often transport the gas to be measured to the sensor or sensors for property measurements using a pump. The pumps used to drive the gas are often bulky and consume large amounts of power. This often limits the application of such systems. In addition, many such sensor systems have a single pump for driving the gas to the sensors. As such, the failure of the pump may cause the entire system to fail.

SUMMARY OF THE INVENTION

The present invention provides an integrated pump and sensor for improved detection and reliability. Preferable, many micro-pumps are provided wherein each micro-pump is in fluid communication with one or more miniature sensors. More preferably, the micro-pumps are mesopumps formed using MEMS technology, wherein each sensor has a dedicated and often individually controllable pump. Such pump/sensor systems can be easily mass produced into a 3D array of integrated lightweight pump-sensors systems. Such system can be used in many applications, including medical gas phase diagnosis, industrial control sensing, agriculture measurements, landmine detection, harmful chemical and biological agent detection, etc.

An illustrative embodiment of the present invention provides an integrated mesopump-sensor assembly suitable for disposition within two- and three-dimensional arrays having small dimensions. One mesopump is formed of an electrostatically attractable flexible diaphragm disposed through cavities or pumping chambers formed between two opposing electrostatically chargeable layers.

The mesopump may be formed of a first, upper layer of a dielectric material having a concave cavity formed in the material lower surface, the cavity having a conductive layer covered by an insulating dielectric layer. A second, lower layer of similar construction may be disposed beneath the first layer in an opposing orientation such that the two concave cavities form a pumping chamber. An interposing layer of a flexible electrically conductive diaphragm material is provided between the upper and lower layers. The diaphragm could be made of insulating material covered on both sides with conductive layers. The flexible diaphragm is attracted toward either the upper or lower layer by applying an electrical potential to either the upper or lower layer conductive portion relative to the interposing diaphragm layer.

Another (second) layer of pumping chambers may be formed by forming concave cavities in the lower surface of the second layer, followed by a second diaphragm layer, followed by an opposing third layer having opposing concave cavities to form a second level of pumping chambers, as further described below. During operation, fluid to be sensed is passed from a first pumping chamber downward to a second chamber, laterally to a third chamber, upward to a fourth chamber, and out through an outlet conduit.

One group of sensors includes chemo-resistive sensors that vary in electrical resistance and/or impedance in response to the presence of an analyte. Various chemo-resistive sensors may vary in composition such that the sensor outputs vary in response to the presence of an analyte from sensor to sensor. The outputs of such single sensors may be unable to identify a particular analyte, but can be collectively analyzed according to Principle Component Analysis (PCA) techniques to identify particular compounds. The multiplicity of sensors that can be provided by two- and three-dimensional arrays of mesopump sensors are well suited to the multiple inputs used by PCA.

Another type of suitable sensor utilizes chemo-fluorescent compounds which fluoresce in response to the presence of general or particular compounds. Many other sensor types are suitable for use with the present invention, including spectroscopic sensors over either broad or narrow wavelengths.

The mesopump-sensors can be arrayed into stacks and coupled to controllers, including micro-controllers or general purpose computers. Computer programs or logic within the controllers can be used to sequence the operation of the pumping chambers and to analyze the sensor outputs. One embodiment includes controller programs that perform PCA. Controller programs can be utilized to operate pump sequencing in either bi-directional or uni-directional modes, depending on the limitations of the mesopumps and on the intended application. Bi-directional modes of operation can be used to push and pull fluid to be sampled past the sensor and can also be used to economize on the number of chambers needed to form a pump channel.

In one mode of operation, a bi-directional "shallow breathing" mode is utilized to draw a fluid such as air into the mesopump-sensor just past the sensor, then expel the fluid so as to minimize any fouling of the mesopump interior past the sensor. Bi-directional modes of operation can also be used to attempt to clean filters of particles and to push clean, purged air past a sensor, where the sensor may have become saturated. Filters may be provided on one or all external fluid orifices, and may include an impactor type filter to trap particles that have entered the mesopump.

The integrated mesopump sensors can provide a large number of small, lightweight, and closely spaced sensors that can be used advantageously to detect airborne agents, including harmful chemical and biological agents or trace amounts of TNT or other explosives from buried land mines. The large numbers of individually controllable sensors also may provide a system that can sequentially operate sensors that are likely to become saturated or poisoned, and to activate pumping and detailed sensing only in response to general sensor outputs or triggers.

DETAILED DESCRIPTION OF THE INVENTION

Figure 1:
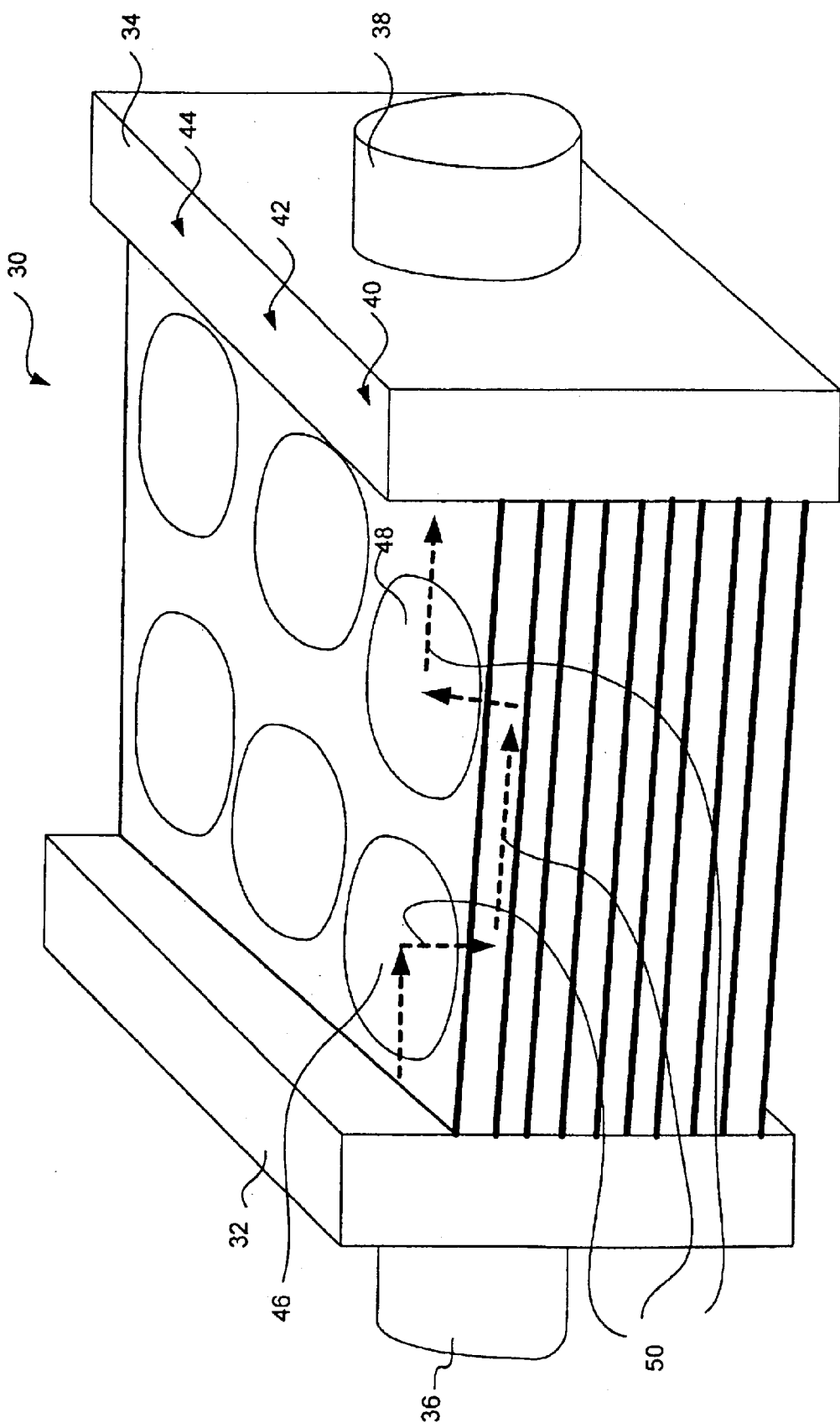
FIG. 1 is a perspective view of a three-dimensional stack of mesopumps having ten pumping levels with three pump channels per level and pneumatic connectors at either end.

FIG. 1 illustrates a mesopump block device 30 having an inlet header 32 and an outlet header 34 including an inlet pneumatic connection 36 and an outlet pneumatic connection 38. Each pump preferably is a mesopump, such as described in U.S. Pat. No. 5,836,750, which is incorporated herein by reference.

Mesopump device 30 includes a first pump channel 40, a second pump channel 42, and a third pump channel 44. In the embodiment illustrated, each pump channel includes a series of four pumping chambers for pumping fluid from the inlet to the outlet. First pump channel 40 includes a first pump chamber 46, a second pump chamber disposed beneath chamber 46 (not shown in FIG. 1), a fourth pump chamber 48, and a third pump chamber disposed beneath fourth pump chamber 48 (not shown in FIG. 1). Arrows 50 show generally the fluid flow through first pump channel 40, illustrating flow through first pump chamber 46, the second pump chamber, the third pump chamber, and fourth pump chamber 48. Fluid can also flow through second pump channel 42, and third pump channel 44 in a similar manner from inlet to outlet.

In the embodiment illustrated, there are ten pump channel levels stacked on top of each other. Each pump channel level includes two chamber levels. In this embodiment, there are three pump channels disposed side by side. Each pump channel is two pumping chambers deep. Mesopump 30 is formed of a three by ten (3×10) stack, meaning that the device is three pump channels in width and ten pump channels in depth. The 3×10 stack of mesopumps may be less than about one inch in any dimension.

As viewed in FIG. 1, the back side of a concave pumping chamber such as chamber 46 is disposed toward the top or outside of the device. In other words, where the planes are formed of a transparent material, the back or convex side of the pumping chamber is displayed toward the outer surface, with the concave surfaces of two opposing faces facing each other to form a pumping cavity.

Figure 2:
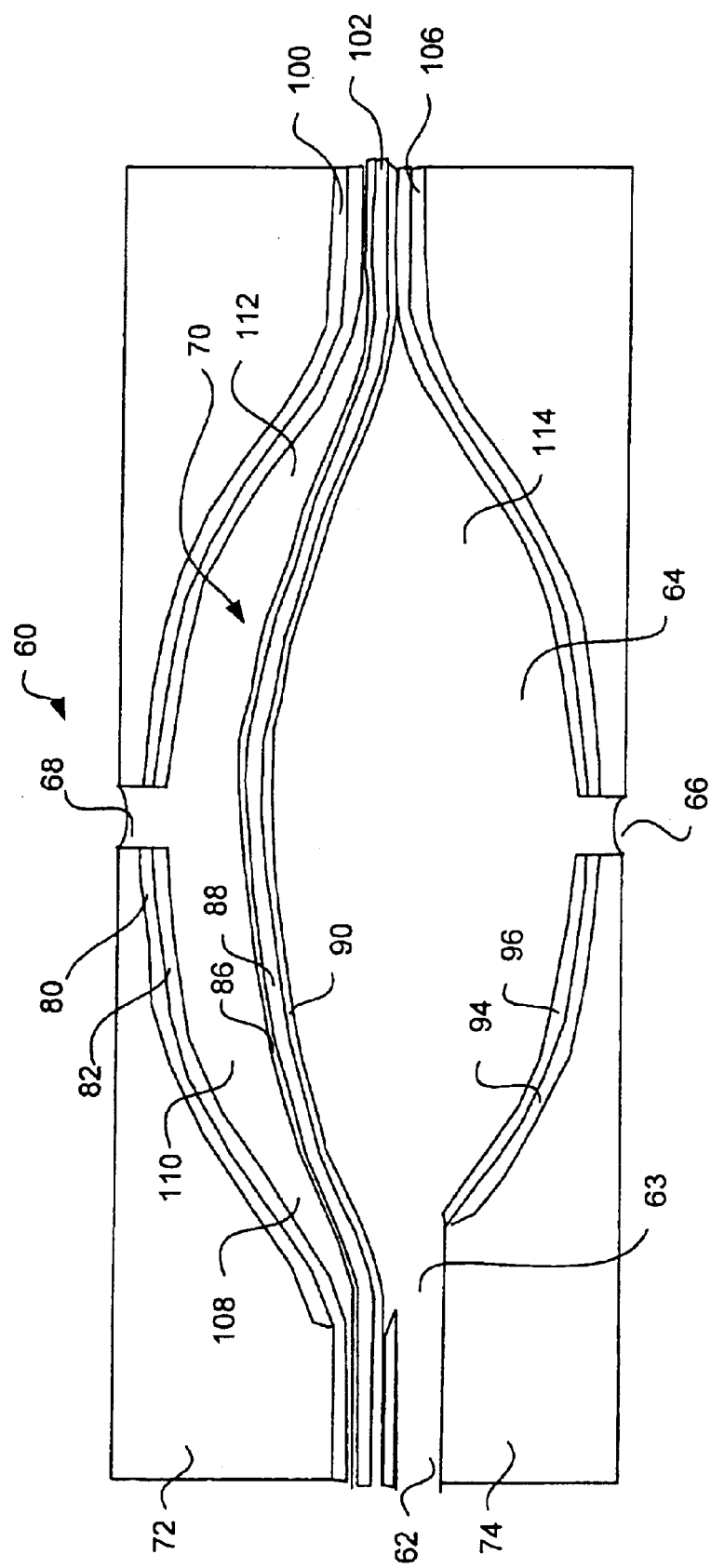
FIG. 2 is a longitudinal, cross-sectional view of a single mesopump pumping chamber formed of a top concave layer, a bottom concave layer, and a flexible diaphragm disposed therebetween.

FIG. 2 illustrates a longitudinal cross-sectional view of a single pumping chamber 60. Chamber 60 includes generally an inlet 62, a cavity 64, an inter-chamber conduit 66, and a back pressure vent 68. Disposed within cavity 64 is a flexible diaphragm 70.

Pumping chamber 60 includes generally a first or top layer 72 and a second or bottom layer 74 and can be about 10 millimeters in diameter in one embodiment. First layer 72 includes a conducting layer 80 and dielectric layer 82. Pumping chamber 60 can be formed by sandwiching together or layering first layer 72 over diaphragm 70 over second layer 74, thereby trapping diaphragm 70 between the upper and lower layers. First layer 72 and second layer 74 can be formed of materials such as polycarbonate or polyetherimide and can be about 0.5 millimeters thick in one embodiment.

Diaphragm 70 can include a first dielectric layer 86, an inner flexible layer 88 having one or more conducting surfaces, and a lower insulating or dielectric layer 90. Diaphragm 70 can be formed of a flexible material such as polyimide or polyester. In one embodiment, diaphragm 70 is formed of commercially available material such as KAPTON™, available from E. I. du Pont de Nemours & Co., Wilmington, Del. or some other metalized polymer film, and is about 25 micrometers thick.

Second layer 74 can also include a conducting layer 94 and an insulating or dielectric layer 96 disposed over conducting layer 94. Conducting layers 80 and 94 can, for example, be a metallic film such as aluminum formed by printing, plating, sputtering, evaporation, or EB deposition of metal, followed by patterning using dry film resist if needed, as is well known in the art. In one embodiment; shadow masks are used to pattern the deposition of evaporated metal to form layers 80 and 94. In one embodiment, aluminum is deposited at a thickness of about 100–500 Angstroms. A similar conducting material can be deposited upon the flexible diaphragm 70.

Dielectric material can be deposited through a thin film deposition process such as sputtering, ion beam sputtering, evaporation, and spin coating. The insulating material can be formed of material similar to the diaphragm material, such as polyimide or polyester. In one embodiment, the flexible diaphragm layer 88 can be about 25 microns and have an aluminum layer on each side of about 100 Angstroms thick.

In the embodiment illustrated, a first layer electrode 100 is coupled to the first layer conductive surface 80. A diaphragm electrode 102 is connected to the diaphragm conductive material 88, and a second layer electrode 106 is electrically coupled to second layer conductive layer 94. These electrodes may be used to create an electrical potential between the first layer conductive surface 80 and diaphragm conductive material 88, or between the second layer conductive surface 94 and the diaphragm conductive material 88. When a potential is created between diaphragm electrode 102 and first layer electrode 100, diaphragm 70 will be electrostatically attracted to first layer 72. The dielectric or insulating layers or coatings upon first layer 72 and diaphragm 70 serve to prevent a short between the diaphragm and the first or second layers when the diaphragm is pulled against first layer 72 or second layer 74.

In FIG. 2, the diaphragm 70 is in closer proximity to first layer 72 at a location nearer the end of the pumping cavity such as at 108, than at a location more centered in the pumping cavity such as at location 110. Thus, when the electrical potential is established between diaphragm 70 and first layer 72, the location of diaphragm 70 nearest the ends of cavity 64 is pulled more strongly than the more central portions of the diaphragm. This causes the flexible diaphragm to be pulled in a wave resembling a peristaltic wave closing contact sequentially from the outer most to the inner most locations of cavity 64.

Cavity 64 is divided into a top cavity portion 112 and a bottom cavity portion 114 by diaphragm 70. When diaphragm 70 is moving upward, fluid is forced outward through back pressure vent 68, wherein the fluid is normally ambient air. When diaphragm 70 is forced downward toward second layer 74, fluid will normally flow downward through back pressure vent 68 and into top cavity portion 112. At about the same time, the fluid of interest, such as air to be sampled, will be forced downward through inter-chamber conduit 66. Thus, the ambient air that flows through the back pressure vent 68 is makeup air that alleviates any vacuum formed in top chamber portion 112.

In the embodiment illustrated, diaphragm 70, when pulled downward toward second layer 74, may immediately force some fluid into inlet aperture 63 extending into cavity 64. Thus, some of the fluid of interest may initially be urged back through inlet 62. However, diaphragm 70 will soon seal fluid inlet aperture 63, preventing any further back flow of fluid other than through inter-chamber conduit 66.

Figure 3:
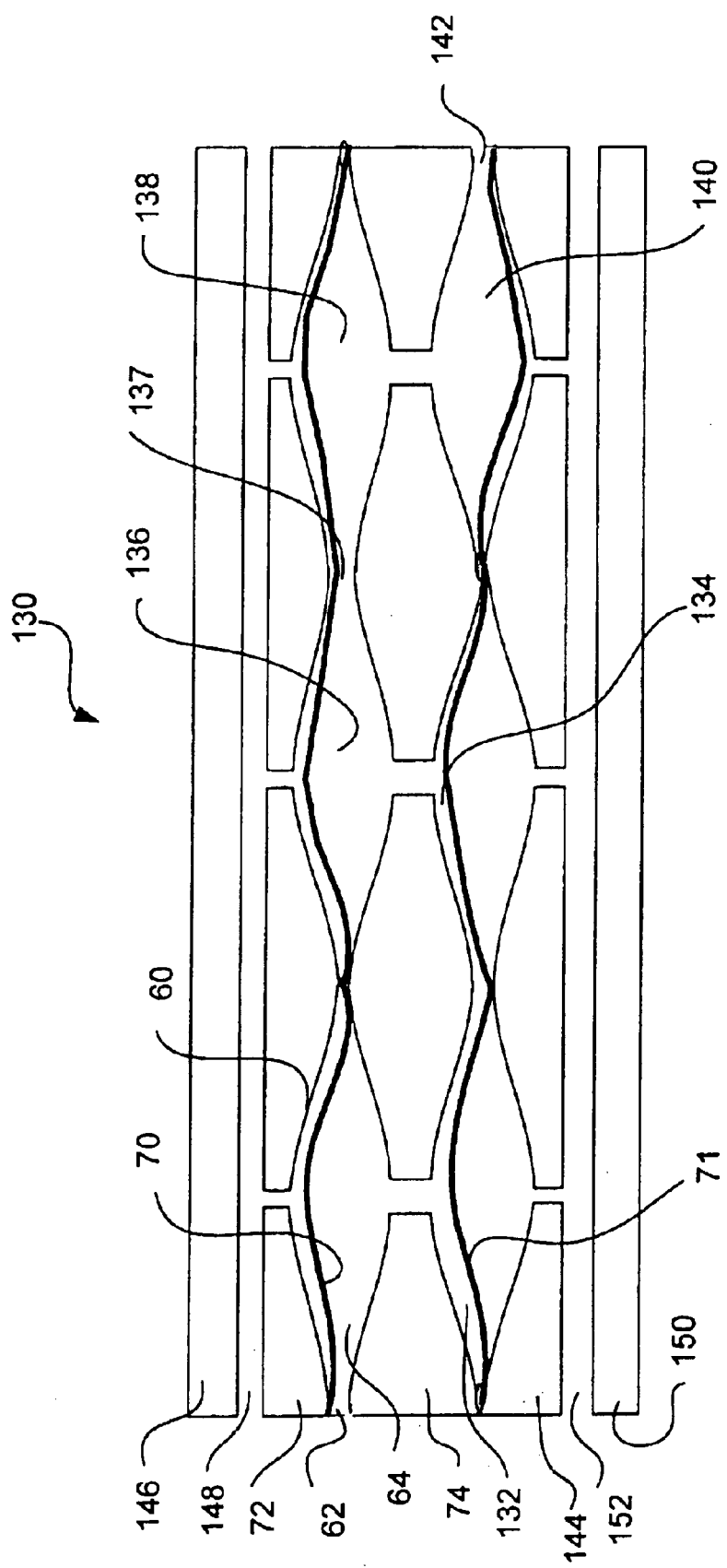
FIG. 3 is longitudinal, cross-sectional view of a mesopump pumping level having a top chamber level and a lower chamber level, each having three pumping chambers.

FIG. 3 further illustrates chamber 60 disposed within a pump channel 130, having two chamber levels with three chambers in each chamber level. The fluid flow may be seen to flow from inlet 62, into first cavity 64, into a second cavity 132, into a third cavity 134, into a fourth cavity 136, into a fifth cavity 138, into a sixth cavity 140, and exiting through an outlet 142. Conduit 137 is a chamber interconnect between cavities 136 and 138. Thus, six cavities are used in series to form one mesopump.

Pump channel 130 is formed of first layer 72, first diaphragm layer 70, second layer 74, second diaphragm layer 71, and third layer 144. Thus, three material layers and two diaphragm layers serve to form the pump channel. A fourth layer 146 may be disposed on the outside of first layer 72 forming a first back pressure channel 148. Likewise, a fifth layer 150 may be disposed on the outside of third layer 144 to form a second back pressure channel 152. Back pressure channels 148 and 152 can serve to provide the makeup air and air to be expelled from the back side of the diaphragm used in the pump. It is contemplated that a separate layer may not be required, as the back pressure channels may be formed directly into or within the first and/or third layers.

Figure 4:
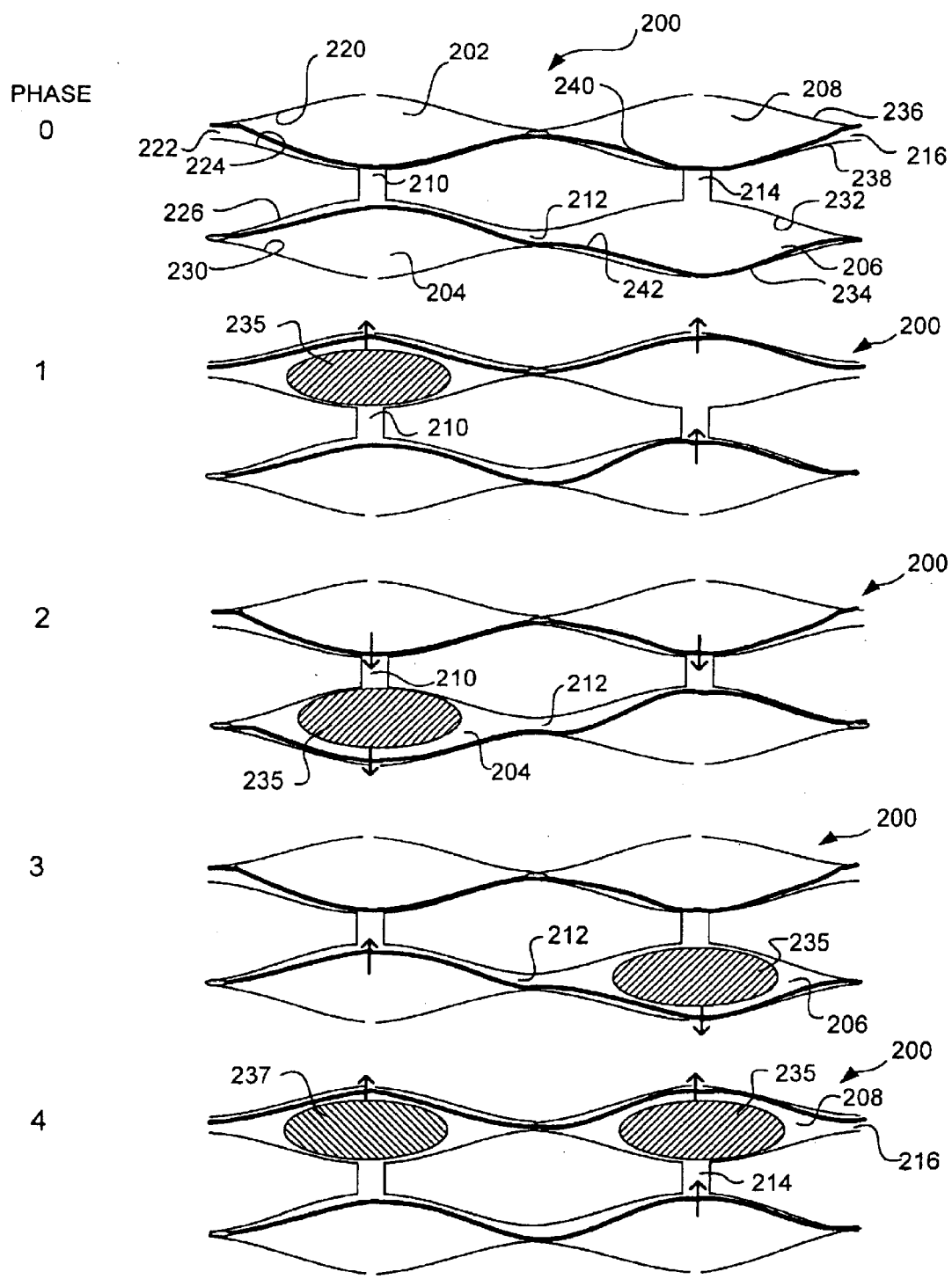
FIG. 4 is a fragmentary, highly diagrammatic longitudinal cross-sectional view of a mesopump pumping level having four electrostatic pumping chambers, illustrating a sequence of events used to pump fluid through the mesopump.

FIG. 4 illustrates a single, double chamber level pump channel 200. Pump channel 200 is illustrated in a highly diagrammatic form to illustrate the operation of the pumping chambers. Pump channel 200 includes a first pumping chamber 202, a second pumping chamber 204, a third pumping chamber 206, and a fourth pumping chamber 208. The fluid flow to be sampled or moved may be seen to flow from an inlet 222, through first chamber 202, through a chamber interconnect conduit 210, into second chamber 204, exiting second chamber 204 through conduit 212, entering third chamber 206, exiting third chamber through inter-chamber conduit 214, entering fourth chamber 208, and exiting through exit conduit 216. In one embodiment, mesopump 200 includes a first diaphragm 240 extending through first chamber 202 and fourth chamber 208. Mesopump 200 also includes a second diaphragm 242 extending through second chamber 204 and third chamber 206. In one embodiment, each diaphragm is formed of a single continuous piece of material extending through two chambers.

First chamber 202 includes an upper conductive surface 220 and a lower conductive surface 224. Second chamber 204 includes an upper conductive surface. 226 and a lower conductive surface 230. Third chamber 206 includes an upper conductive surface 232 and a lower conductive surface 234. Fourth chamber 208 includes an upper conductive surface 236 and a lower conductive surface 238. The conductive surfaces are preferably coated with a dielectric layer. In one embodiment, the diaphragm is moved by maintaining the diaphragm conductive potential at ground or neutral and applying an electrical potential to the upper or lower surface of the pumping chamber. For example, the portion of diaphragm 240 within pumping chamber 202 can be moved upward by applying an electrical potential to upper conductive surface 220. Diaphragm 240 can be pulled downward within pumping chamber 202 by applying an electrical potential to bottom conductive surface 224.

FIG. 4 illustrates mesopump 200 in five different phases, three of which are distinct. Beginning with phase 0, an initial phase, diaphragm 240 may be seen to be in a lower position within both first chamber 202 and fourth chamber 208. Lower diaphragm 242 may be seen to be in an upper position within second chamber 204 and a lower position within third chamber 206.

In transitioning to phase 1, an electrical potential may be applied to first chamber upper surface 220, third chamber upper surface 232, and fourth chamber upper surface 236. As indicated by arrows in phase 1, diaphragms within first chamber 202, third chamber 206, and fourth chamber 208 move upward. This movement within first chamber 202 pulls the fluid to be sampled into first chamber 202, indicated by cross-hatched area 235 within first chamber 202.

In transitioning to phase 2, electrical potential can be applied to the lower surfaces of the first, second, and fourth chambers. This can act to move the diaphragm downward to the lower surfaces of the first, second, and fourth chambers. The fluid sample of interest 235 is pushed and pulled downward from first chamber 202 into second chamber 204. This occurs because of the downward force of upper diaphragm 240 and the vacuum or pulling effects of lower diaphragm 242. While some fluid may be initially expelled through inlet 222, as previously explained, the peristaltic action of upper diaphragm 240 acts so as to close off any fluid exit through inlet 222.

In transitioning to phase 3, an electrical potential can be applied to upper surface 226 of second chamber 204 and lower surface 234 of third chamber 206. While first chamber 202 remains sealed by the lower position of upper diaphragm 240, the upward movement of lower diaphragm 242 acts to force the fluid of interest through conduit 212, into a third chamber 206. In one embodiment, lower diaphragm 242 is affixed to a lower surface of conduit 212, thereby forming a flow passage above the diaphragm.

In transitioning to phase 4, an electrical potential may be applied to upper surface 220 of first chamber 202, upper surface 232 of third chamber 206, and upper surface 236 of fourth chamber 208. The fluid of interest is thus pushed up by lower diaphragm 242 and pulled by upper diaphragm 240 into fourth chamber 208. At the same time, a new fluid sample 237 of interest may be pulled into first chamber 202 by the upward movement of upper diaphragm 240 within first chamber 202. As may be seen from inspection of FIG. 4, phase 3 is similar in diaphragm positions to phase 0, and phase 4 is similar in diaphragm positions to phase 1.

In a subsequent phase, such as the immediate next phase, the fluid sample of interest 235 can be expelled from fourth chamber 208 through exit outlet 216. In embodiments having more than four chambers, the fluid expelled from fourth chamber 208 can be expelled into another chamber. In this way, a long pipeline of chambers can be formed for various purposes.

In some embodiments, after pulling in a fluid sample of interest, the logic operating mesopump 200 can be used to expel the fluid from fourth chamber 208 back into third chamber 206, thence into second chamber 204, into first chamber 202, and out inlet conduit 222. This is but one way in which mesopump 200 can be operated in a bi-directional manner. If desired, samples may be held for long time periods within the samples of the mesopump by simply trapping a sample in one of the chambers. This may be desirable where further analysis is desired for one of the fluid samples.

Figure 5:
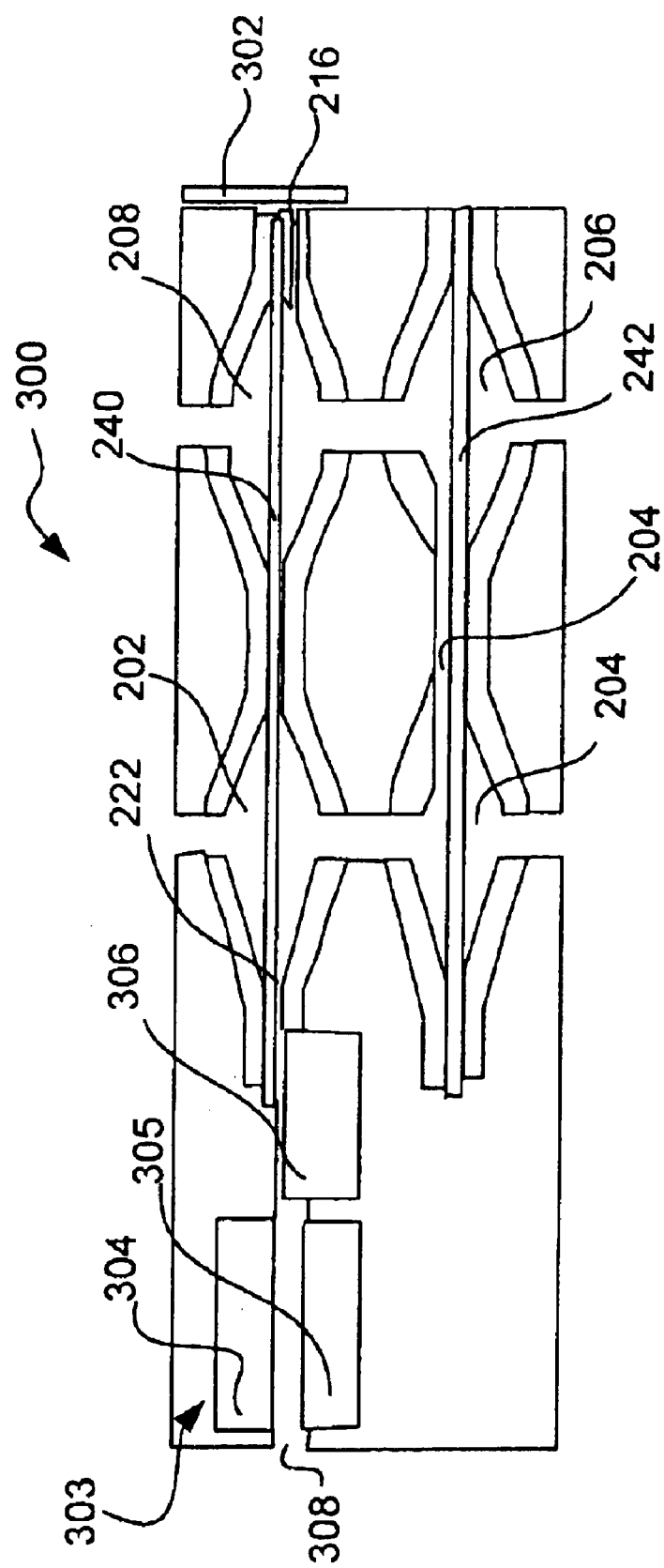
FIG. 5 is a longitudinal cross-sectional view of an integrated mesopump-sensor, wherein the sensor is disposed near a fluid intake channel to the mesopump.

Referring now to FIG. 5, an integrated mesopump-sensor 300 is illustrated, including some elements previously described in FIG. 4 with respect to mesopump 200 and utilizing the same reference numerals to aid in understanding the integrated mesopump-sensor. Material layers adjacent to the layers forming the top and bottom of the pumping chambers which can form the makeup and vent air channels are not shown in FIG. 5.

Mesopump-sensor 300 includes first chamber 202, second chamber 204, third chamber 206, and fourth chamber 208. Air or another fluid to be sampled can flow through an intake 308, past a sensor 303, through a first filter 306, through inlet 222, through the four pumping chambers, through outlet 216, and through a second filter 302.

Sensor 303 is represented diagrammatically as an object enclosing the fluid intake channel to the mesopump portion in FIG. 5 and having a first part 304 and a second part 305. In one embodiment, sensors are placed on the walls of narrow individual flowing channels so as to maximize the surface-to-volume ratio and maximize the interaction between analyte and sensor material. The type of sensor used as sensor 303 can be varied according to the application.

In one embodiment, sensor 303 is a chemoresistive sensor that varies in resistivity or impedance depending on the amount of analyte present in the fluid sample and adsorbed onto the sensor. In some embodiments, the sensor is formed of a polymer and a plasticizer, with the plasticizer varied in composition across multiple integrated mesopump sensors to give multiple readings for a fluid sample that is believed to be similar across multiple sensors. In one example of a chemoresistive sensor, electrically conductive polymer elements include a polymer film which swells upon exposure to an analyte which can induce changes in resistivity and/or impedance in the polymer film, enabling direct low power electrical signal readout to be used as the sensing signal.

Processable thin films of electrically conducting organic polymers can be prepared on the individual sensor elements. The processable films can be plasticized during deposition, providing diversity and systematic control over the chemical bonding properties of each of the chemoresistor elements. For example, various non-conductive polymers such as polystyrenes can be dissolved in tetrahydrofuran (THF) and carbon black suspended in the mixture, which can then be applied to interdigitated electrodes and the THF allowed to evaporate, leaving a polymer film. Each polymer can have a different resistivity response to an adsorbed analyte. In another example, the same polymer can be mixed with various plasticizers to create the sensors, with the resistivity response varying according to the plasticizer used. In one such example, poly(pyrrole) can have various plasticizers added to create different sensors. See, for example, U.S. Pat. Nos. 5,571,401 and 5,911,872, and Proc. Natl. Acad. Sci., USA, Vol. 92, No. 7, pp. 2652–2656, March 1995, which are all incorporated herein by reference.

In some embodiments, the sensors do not individually identify chemical species, but may create a multiple-dimensioned output that can be used to identify the analyte. In particular, Chemometric or Principle Component Analysis (PCA) methods and software may be used to identify a chemical or biological species or at least a genus. PCA methods are well known, see for example Chemometrics and Intelligent Laboratory Systems 1 & 2, pub. Elsevier Science Publishers (1986 & 1987), or Chemometrics, A Practical Guide, Beebe et al., pub. Wiley & Sons. Both of the aforementioned books are incorporated herein by reference. The present invention can support the presence of arrays of different sensors all within a small volume. The large number of differing lightweight and small volume sensors supported by the present invention can provide for PCA identification within handheld field units not previously practicable.

In some embodiments, sensor 303 may include a heater or have a heater upstream to warm the fluid to be measured and/or the sensor itself to an appropriate temperature. One use of the heaters is to warm a polymeric sensor to desorb any adsorbed or absorbed analyte. For example, after a time period and/or a cumulative amount of analyte exposure, the mesopump logic can be set to purge the sensor with a relatively clean fluid and/or heat the sensor directly or indirectly to desorb the analyte from the possibly saturated sensor. After a time period and/or sensor output indicates that the sensor is likely desaturated, a normal sensing mode may be entered. In one embodiment, the heater is deposited directly on a capillary tube used as a substrate for the sensing polymer. In another embodiment, the heater is embedded in a substrate that surrounds the sensing polymer. In yet another embodiment, the heater is placed upstream to heat the air or fluid that subsequently flows over the polymer.

Other examples of sensors suitable for sensor 303 include analyte specific sensors which primarily or exclusively identify a single species or a narrow genus of chemical or biological agents. In one embodiment, a fluorescent sensor be used which varies in fluoresce and quenching in response to the presence of trace amounts of an agent which, in some embodiments, include TNT and DNT. For example, certain pentiptcene derived conjugated polymers can provide an excellent and highly sensitive fluorescence chemosensor for the detection of electron-deficient unsaturated species including TNT, DNT and BQ. Detection of TNT, in particular, can be utilized in landmine detection. See J. Am. Chem. Soc., Vol. 120, No. 21, pp. 5321–5322 (1998), and J. Am. Chem. Soc., Vol. 120, No. 46, pp. 11864–11873 (1998), both of which are incorporated herein by reference.

Light may be provided by sensor first part 304, and absorbed by and fluoresced from sensor part 305 having a fluorescing agent, and detected by a detector in either first part 304 or second part 305. In one general embodiment, the sensor may be a chemo-optical sensor. The absorbance of the carrying fluid and sample may be measured, with sensor first part 304 having an emitter and sensor second part 305 having a detector. Infrared or near infrared absorbance may be used, with each sensor 303 detecting absorbance at a different wavelength.

Mesopump sensor 300 can be operated either uni-directionally or bi-directionally, and can utilize the filter illustrated or utilize different filters. In one method, mesopump sensor 300 is operated in a uni-directional manner, with the fluid to be sampled, such as air, taken in through port 308, past sensor 303, through filter 306, through the pumping chambers, and out through filter 302. In this mode of operation, the first filter 306 may serve to keep particles out of the pumping chambers. In a second uni-directional mode of operation, fluid to be sampled may be taken in through second filter 302, through the pumping chambers, past first filter 306, and past sensor 303. In this mode of operation, second filter 302 may act to screen contaminate particles such as dust from entering the pumping chambers, and first filter 306 can act to screen finer contaminate particles from nearing the sensor. In this mode of operation, if the filters become sufficiently clogged so as to impair the operation of the mesopump sensor, various modes of handling the clogging are available, depending on the contaminant, the filter, and the sensor.

In one mode of operation, the clogged pump channel is shut down, and a fresh pump channel is put on line to take over the function. This mode of operation illustrates one advantage of the present invention, where tens, hundreds, or even thousands of the sensors may be available to take over ad seriatim, each for a period of time or cumulative loading. In another mode of operation, the clogged pump channel can be operated in reverse to backwash the filters in an attempt to force the contaminants from the filters. This mode of operation may be more successful where the air to be used to backwash the filters is either purified or filtered, or the contaminants are such as can be removed from the sensor during normal air flow and do not irreversibly adhere to or otherwise poison the sensor. In yet another mode of operation, filters may be provided on either end of the mesopump pump channels, such that pumping in a first direction traps dust in a first filter and backwashes the second filter, and the reverse occurs in the reverse pumping direction. Filters can be made of many materials including Porex® Porous Plastics such a polyethylene or polypropylene sheets, available from Porex Technologies Corp, Fairborn Ga.

As indicated above, the mesopump may be operated in a bi-directional manner so as to prevent the sensor from becoming saturated with the analyte or other material. In one example, mesopump 300 is operated in a measuring mode in a first direction, bringing in air through port 308 and expelling air through port 216. At a point where sensor saturation is believed possible, the pumping direction can be reversed, operating in a purifying mode, bringing in air through port 216 and expelling air through port 308. In this purifying mode of operation, the air entering through port 216 can either be purified by a filter, such as a charcoal or HEPA filter, or provided with a purified gas source. The purifying mode of operation can be continued until the analyte or other absorbant is believed to have been sufficiently desorbed from sensor 303. The purifying mode of operation can be particularly useful where chemoresistive or fluorescent polymers are used to detect the analytes. In one bi-directional "shallow breathing" mode of operation, the mesopump is operated with the goal of drawing a fluid sample past the sensor, then expelling the fluid sample through the same intake port. In this mode, a goal is to draw the sample past the sensor but not into the mesopump, so as to reduce fouling of the mesopump.

Figure 6:
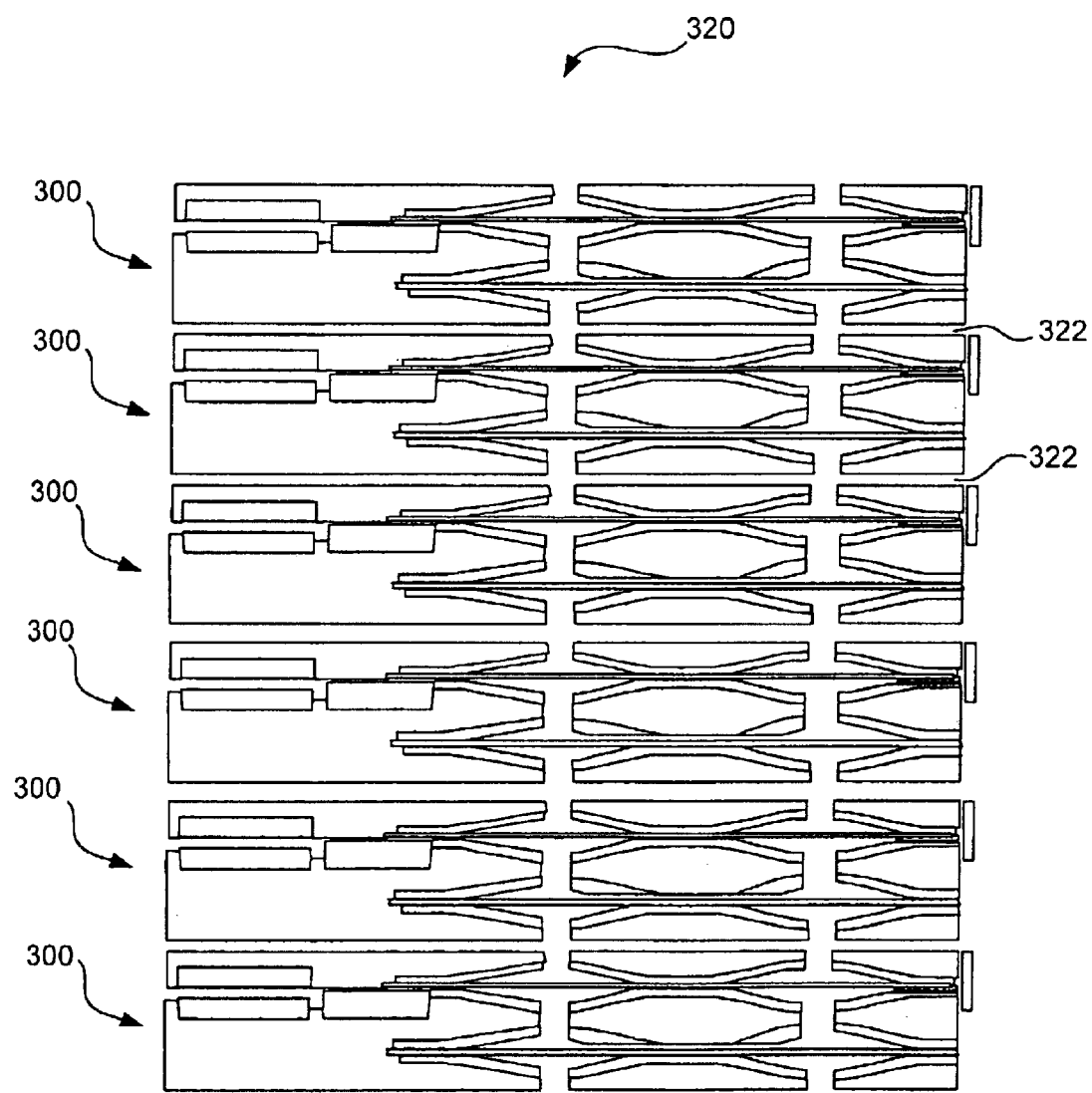
FIG. 6 is a longitudinal cross-sectional view of a stack of six of the integrated mesopump-sensors of FIG. 5.

Referring now to FIG. 6, an array of integrated mesopump-sensors 320 may be seen to be formed of six layers of integrated mesopump sensors 300, as discussed with respect to FIG. 5. In a preferred embodiment, the mesopump-sensors are grouped as a three-dimensional array. The integrated mesopump sensors may be separated by vent channels 322, as discussed with respect to channels 148 and 152 of FIG. 3. The channels may be formed by standoffs, channels formed in the layers, or with separate layers, as discussed with respect to FIG. 3. It may be seen that an array of integrated mesopump-sensors can be formed by layering the pump body layers and the diaphragm layers. It may also be seen that the air intakes or ports are disposed relatively close together, and can be fed by a common header, such as illustrated by intake 36 of FIG. 1. In this way, the air sample reaching each of the sensors may be reasonably expected to be similar in composition at any point in time.

Figure 7:
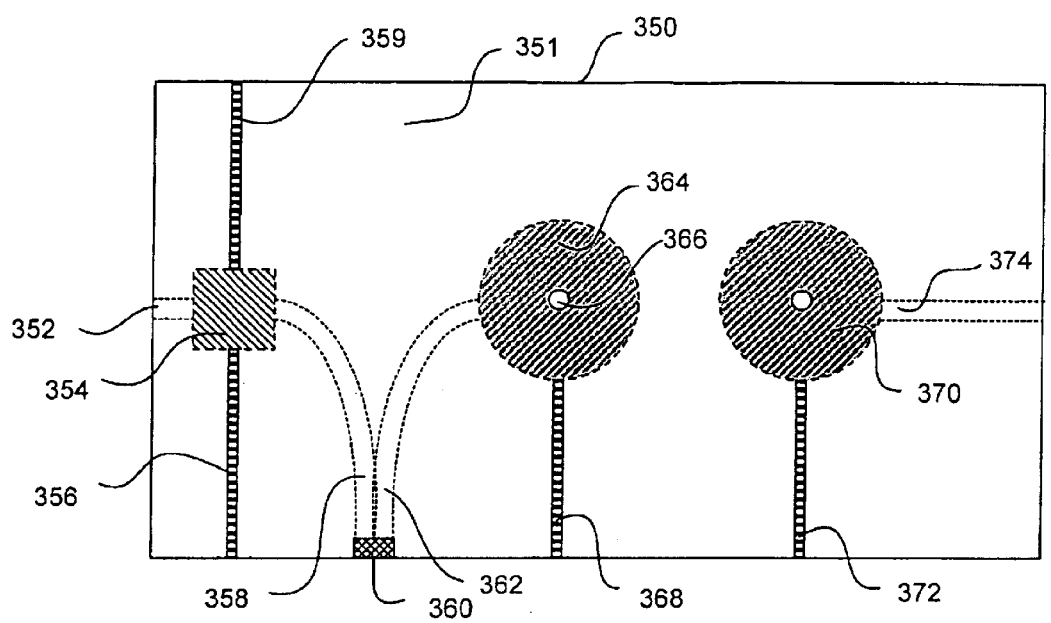
FIG. 7 is a top view of a integrated mesopump-sensor chamber level having a fluid intake, sensor, impactor filter, mesopump, and fluid outlet, with fluid conduits and two chambers shown in phantom.

Referring now to FIG. 7, a single pumping layer or chamber level of an integrated mesopump-sensor 350 is illustrated. The layer of material representing the top layer is represented by reference numeral 351. The elements illustrated in FIG. 7 would lie within a material layer in one embodiment and be visible only if the material forming the top layer were transparent or translucent, which layers formed of polycarbonate may be. Mesopump-sensor layer 350 includes an intake port 352, a sensor 354, and electrodes or optical connection lines 356 and 359. Electrodes 356 and 359 can include connections for supplying power to sensor 354 and for obtaining a signal from sensor 354. In those embodiments having heaters, electrodes 356 and 359 may include an electrical line for powering a heater for the sensor and/or the fluid to be sampled. A fluid conduit 358 continues from sensor 354 in an arc, terminating at an impactor filter 360.

The geometry of arced conduit 358 operates to accelerate any particles within the conduit, causing them to strike the impactor filter, while the carrying fluid, such as air, continues on to a second fluid conduit 362. The momentum of the particles causes them to strike the impactor filter. The impactor filter can be formed of any material suitable for trapping the particles that strike it. One group of suitable materials for forming impactor filter 360 includes adhesives.

Fluid conduit 362 continues on to a first pumping chamber 364, having a vent hole 366 extending up through the top of layer 351. In the view illustrated in FIG. 7, the back side of a concave surface would be visible when the top layer is transparent or translucent. A fourth pumping chamber 370 is also illustrated. In one embodiment, a second pumping chamber is disposed beneath first pumping chamber 364, and a third pumping chamber is coupled laterally to the second chamber with a conduit. In this embodiment, the third chamber can be coupled to fourth chamber 370 via a fluid conduit, as previously described. An electrode 368 may be seen extending from first chamber 364 as well as an electrode 372 extending from fourth chamber 370. Electrodes 368 and 372 can be used to apply an electrical potential to the conductive layers of the chambers and initiate electrostatic movement of the diaphragms, as previously described. Fluid may exit from fourth chamber 370 through another fluid conduit 374. Integrated mesopump-sensor layer 350 can be operated in either a uni-directional mode or a bi-directional mode, depending on the controlling logic.

Figure 8:
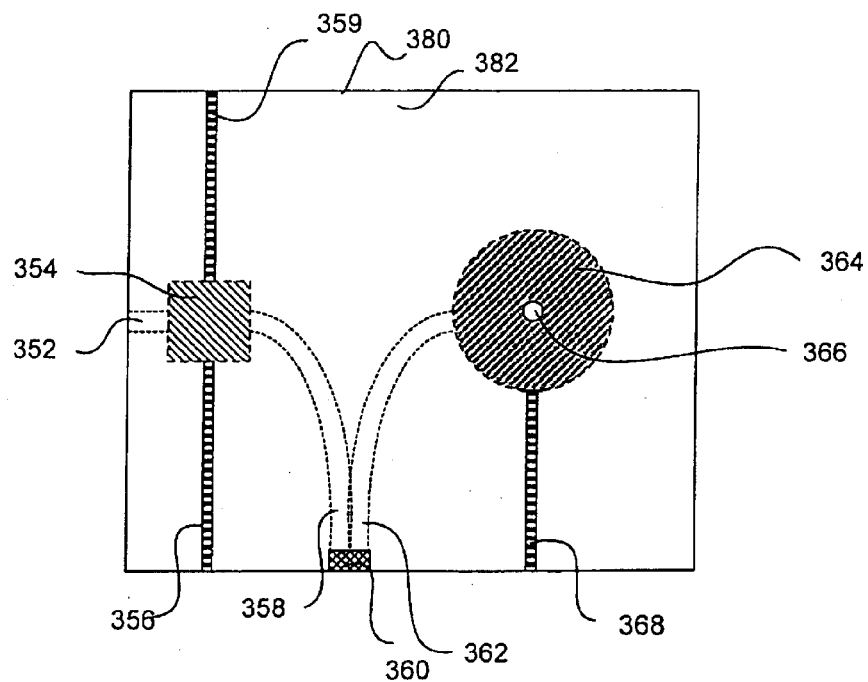
FIG. 8 is a top view of a bi-directional integrated mesopump-sensor chamber level having a fluid intake/outlet, sensor, impactor filter, and mesopump, with fluid conduits and single chamber shown in phantom.

Referring now to FIG. 8, a bi-directional integrated mesopump-sensor level 380 is illustrated, including a pump body layer 382. As described with respect to the embodiment illustrated in FIG. 7, a fluid sample can flow from conduit 352 to impactor filter 360, and to first chamber 364. In this bi-directional embodiment, there is no second conduit to expel the sample fluid apart from conduit 352, requiring this embodiment to operate in a bi-directional mode, rather than having the option of operating in a uni-directional mode. The chamber can be operated so as to bring fluid in past sensor 354 in a first direction, then expel the fluid past sensor 354 in the opposite direction, before bringing in a second sample of fluid.

Figure 9:
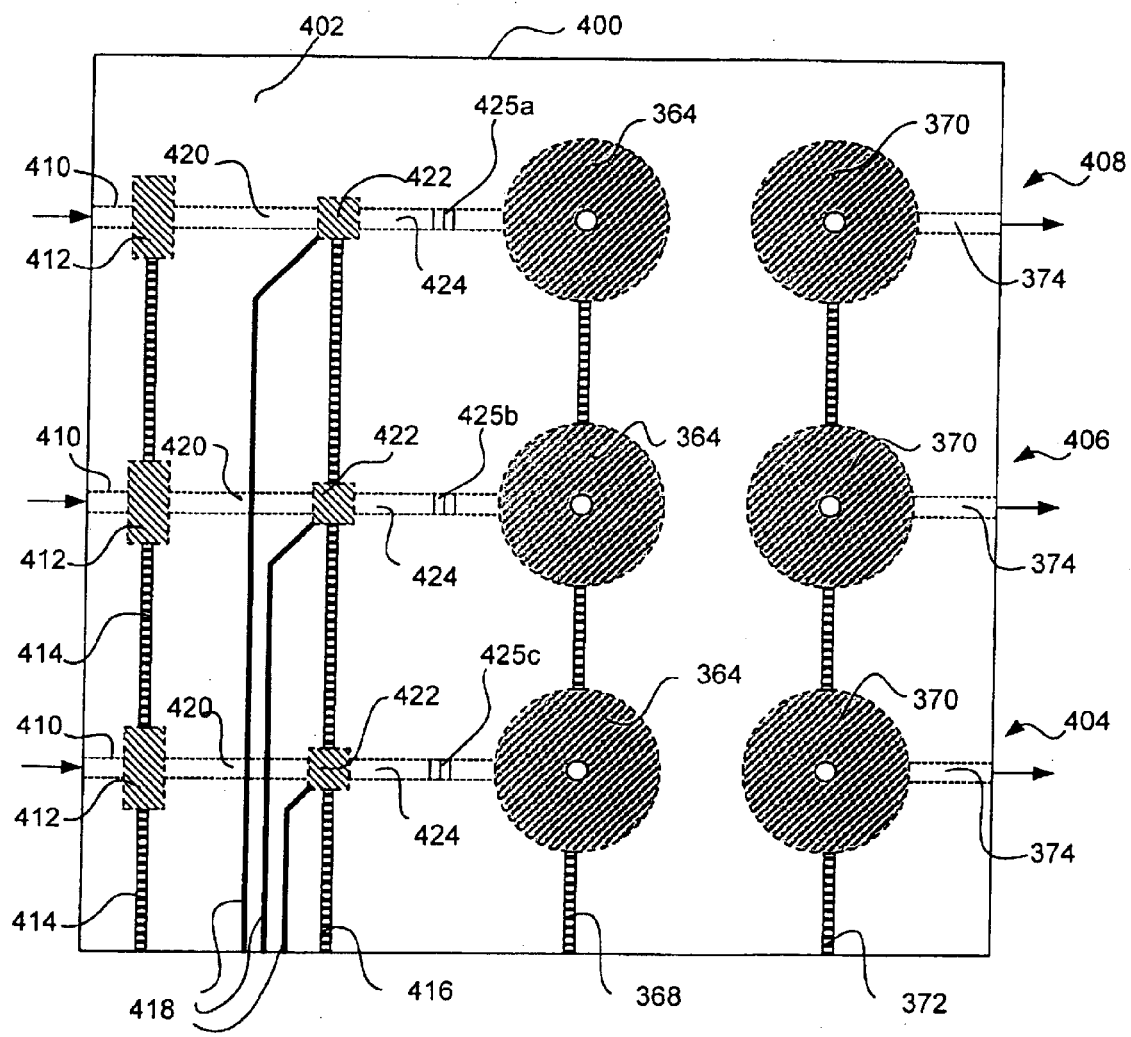
FIG. 9 is a top view of an integrated mesopump-sensor chamber level having three pump channels, each with a fluid intake, heater, sensor, mesopump, and fluid outlet, with fluid conduits and three chambers shown in phantom.

FIG. 9 illustrates a top view of a single integrated mesopump-sensor pumping level 400 having a two-dimensional array of three pump channels each formed of four pumping chambers, two of which are illustrated as visible through a translucent top pumping layer material 402. Pumping level 400 includes a first pump channel 404, a second pump channel 406, and a third pump channel 408. Previously described reference numerals refer to previously discussed elements. In the embodiment illustrated, each pump channel includes a first conduit 410 leading to an excitation source 412, continuing on through a second conduit 420 to a sensor (detector) 422, and further onward to first pumping chamber 364. As previously discussed, the fluid to be sampled can continue on to fourth pumping chamber 370, exiting through conduit 374. In the embodiment shown, the excitation source 412 are heaters powered through heater electrodes 414, and sensors 422 are powered through sensor power electrodes 416, with signals returning through sensor signal electrodes 418.

It is contemplated that flow sensors 425a–c may be provided in the pump channels fro increasing the flow of gas therein. The flow sensors may be microbridge structures of the type as described in, for example, U.S. Pat. Nos. 4,478,076; 4,478,077; 4,501,144; 4,651,564; 4,683,159; and 4,576,050.

Figure 10:
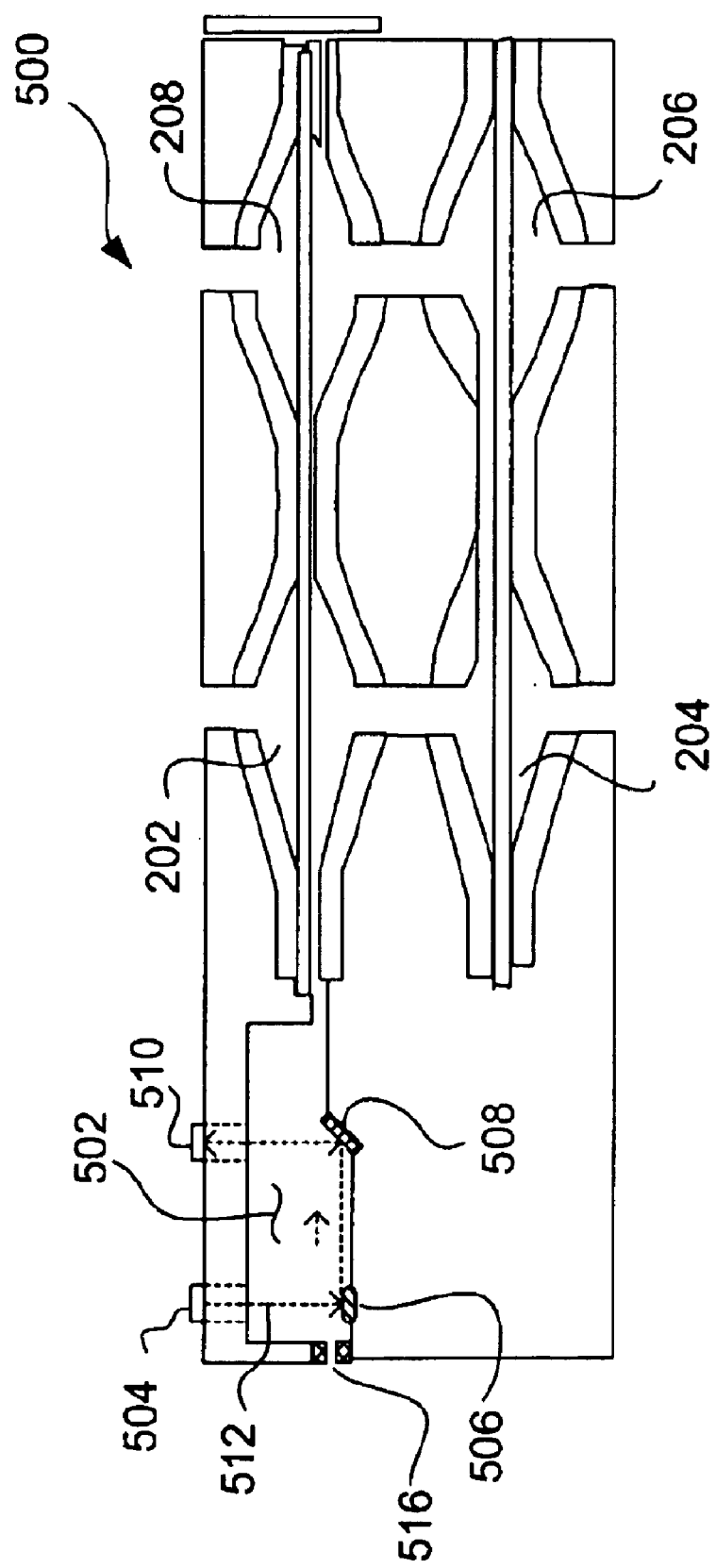
FIG. 10 is a longitudinal cross-sectional view of an integrated mesopump sensor having a top mounted light source and photo detector and an oblique reflecting surface in the fluid pathway.

FIG. 10 illustrates an integrated mesopump-sensor pumping level 500 similar in many respects to mesopump-sensor pumping level 300 illustrated in FIG. 5. Mesopump sensor 500 includes an optical sensing chamber 502 which has light both supplied from and detected by devices disposed on the same side of the level, in this embodiment, on the top side of the pumping level. Optical sensing chamber 502 can be used in conjunction with fluorescing materials sensitive to analytes of interest, as previously discussed. A light emitter 504 emits light downward toward a sensor material 506, such as a fluorescing polymer. Any fluorescence from material 506 is visible to, and reflected by, for example a diagonal reflecting mirrored surface 508 which directs the fluorescence upward to a detector 510. In one embodiment, the diagonal surface is integrally formed into the body of the mesopump-sensor. Light paths are denoted by arrows 512. Positioning the emitter and detector on the same side allows for ease of manufacturing. Sample fluid flow is similar to that previously discussed and can be pulled into and pushed out of an intake 516.

Figure 11:
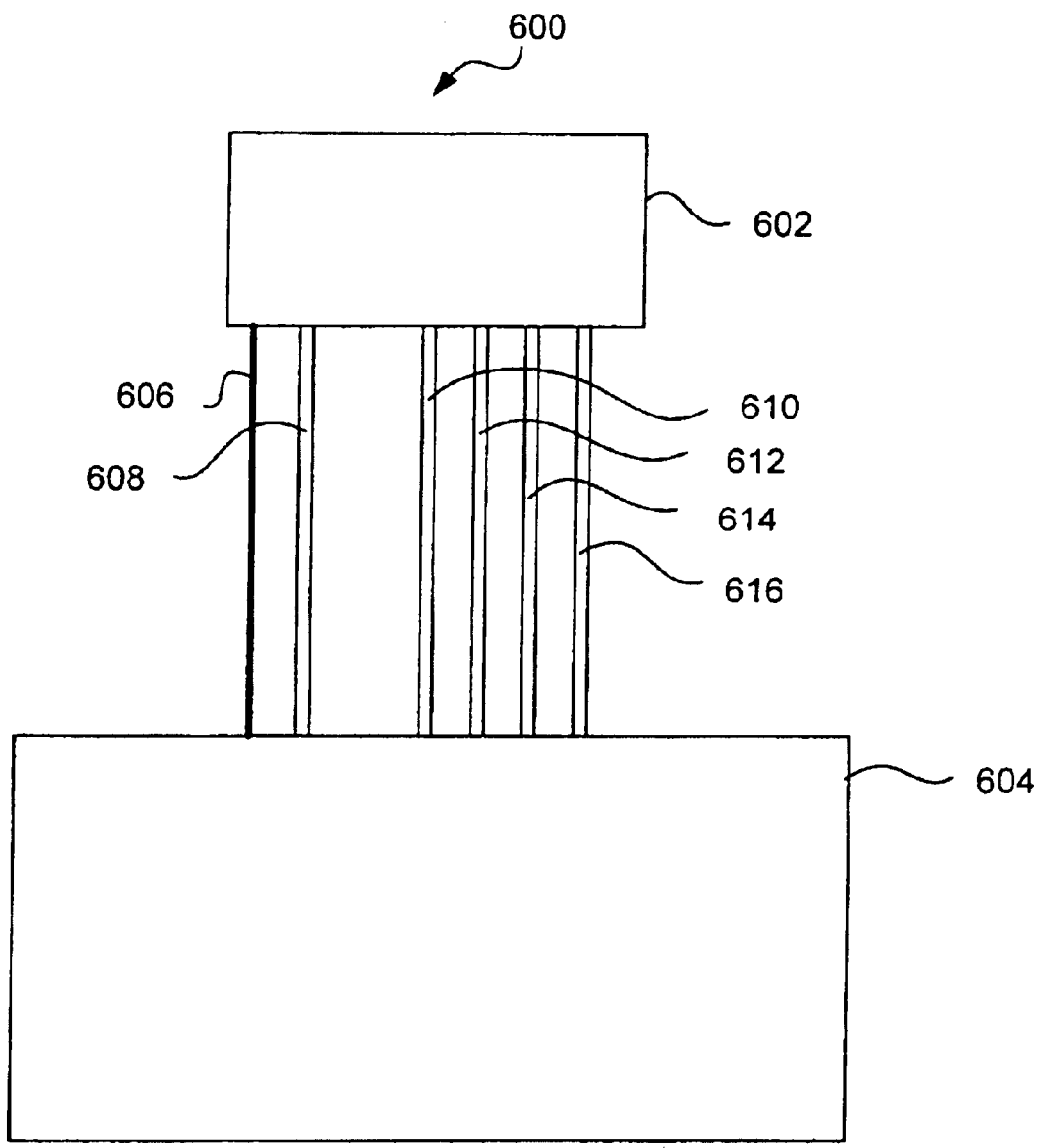
FIG. 11 is a highly diagrammatic view of an integrated mesopump sensor having a controller which can be used for controlling pump sequencing and interpreting sensor outputs.

Referring now to FIG. 11, an integrated mesopump-sensor system 600 is schematically illustrated having a controller 602 electronically coupled to a single mesopump-sensor pump channel 604. Controller 602 can have various integrated or separate display components, not requiring illustration, for displaying the operating status and analyte values. In one embodiment, a plurality of control and sensing lines are coupled to each pumping layer. In the embodiment illustrated, the electronic control and sensing lines include a heater supply electrode 606 and a pair of sensor signal lines 608. Also included in the embodiment illustrated is a pair of control lines for each pumping chamber. Mesopump-sensor layer 604 has four pumping chambers, with pumping control line pairs 610, 612, 614, and 616 being coupled to the first, second, third, and fourth pumping chambers, respectively. In one embodiment, as discussed with respect to FIGS. 2–4, the upper and lower conductive layer in each pumping chamber are connected to a separate electrical potential source. In some embodiments, the diaphragm is electrically at ground, while in other embodiments, the diaphragm is electrically coupled to a separate control line.

Controller 602 can be any suitable device for controlling and sensing the outputs of the mesopump-sensor device. In some embodiments, controller 602 includes a programmable microcontroller, for example a controller in the PIC family of microprocessors. In other embodiments, controller 602 includes microprocessors having a control program stored in firmware which may or may not be re-writable. In still other embodiments, controller 602 includes a general purpose computer with suitable input/output hardware.

Controller 602 is preferably capable of being programmed with a variety of programs, which can be implemented as high-level computer languages, low-level computer languages, and as more direct machine control representations such as Boolean or ladder logic control languages. The control portion of the programs can include timing control portions for controlling the timing of the pumping chamber operation. The timing control may include, for example, a repetitive cycle for controlling the upper and lower potentials of the conductive layers of the pump channels relative to the diaphragms.

It is contemplated that the control program may include logic for reversing the direction of the pumping. This may be used to pull in a clean purging fluid to desaturate the sensor, to move the fluid to be sampled back and forth past the sensor for increased sensitivity, or to backwash the filter in an attempt to clean them.

Some control programs may include activation logic to activate dormant pump channels when other pump channels detect a particular substance, or become saturated or otherwise damaged during operation. For example, the control program may operate pump channels in sequence, putting new pump channels on line after a time period when it is feared that a sensor may be saturated or even poisoned. The control program may also, for example activate or deactivate pumping depending on the applications. One example of such a sensor is the detection of a general class of material by a broad detecting sensor, followed by activation of several sensors and/or more specific sensors to detect a species of interest, such as TNT.

Controller 602 preferably includes analysis programs to analyze the sensor outputs. In one embodiment, neural networks software or hardware is included in controller 602. In another embodiment, chemometric or principal component analysis (PCA) programs are included within controller 602. In still other embodiments, spectroscopic analysis programs are included within controller 602. In embodiments having multiple sensors, each for detecting a small portion of the information needed to identify the analytes of interest, applicants believe that PCA software may be of particular use. In embodiments where controller 602 includes a general purpose computer, a variety of programs may be executed on the controller, many of the programs being user supplied and developed for specific applications.

Numerous advantages of the invention covered by this document have been set forth in the foregoing description. It will be understood, however, that this disclosure is, in many respects, only illustrative. Changes may be made in details, particularly in matters of shape, size, and arrangement of parts without exceeding the scope of the invention. The invention's scope is, of course, defined in the language in which the appended claims are expressed.

What is claimed is:

1. A sensing system comprising:
   an array of integrated cells for the sampling and detection of airborne chemical and biological species; and
   wherein each cell of the array of integrated cells comprises:
      a mesopump comprising a plurality of polymer layers forming a plurality of cavities; and
      a metalized polymer diaphragm situated within each cavity of the plurality of cavities of the mesopump; and
   at least one micro sensor structurally formed within the mesopump.

2. An array of integrated cells as recited in claim 1, wherein selected integrated cells have a first micro sensor type and selected other integrated cells have a second micro sensor type, wherein the first micro sensor type has different sensing characteristics than the second micro sensor type.

3. An array of integrated cells as recited in claim 2, wherein selected integrated cells have a heater means for directly or indirectly heating said micro sensors for desorbing an analyte.

4. A sensing system comprising:
   an array of integrated mesopumps for the sampling and detection of airborne chemical and biological species; and
   wherein each mesopump comprises:
      a first layer, at least a portion of which is electrically chargeable;
      a second layer opposing said first layer, at least a portion of which is electrically chargeable;
      said first and second layers forming a cavity therebetween;
      an electrostatically moveable diaphragm disposed between said first and second layers and disposed through said cavity for pumping fluid through said cavity;
      a flow channel formed into at least one of said first and second layers and in fluid communication with said cavity; and
      a micro sensor embedded in said flow channel and disposed in fluid communication with said flow channel, such that the pumped fluid passes said sensor when pumped into or out of said cavity.

5. The sensing system of claim 4, wherein each micro sensor may be one of a group comprising a chemoresistive sensor, a chemo-optical sensor, and a chemo-fluorescent sensor.

6. The sensing system of claim 4, wherein said first and second layers, diaphragm and flow channel of each mesopump comprises a plastic material.

7. The sensor system of claim 6, wherein said sensor system includes a controller having a program for sequencing the movement of said electrostatically moveable diaphragm of each mesopump to provide either unidirectional or bidirectional flow.

8. A sensing system comprising:
   an array of integrated micro pumps for the sampling and detection of airborne chemical and biological species; and
   wherein each micro pump comprises:
      a plurality of polymer layers forming a plurality of cavities;
      a metalized polymer diaphragm situated within each cavity of the plurality of cavities; and
      at least one micro sensor formed within the plurality of cavities.

9. The sensing system of claim 8, wherein the at least one micro sensor is structurally integrated in each micro pump.

10. The sensing system of claim 8, wherein the at least one micro sensor is embedded in each micro pump.

11. The sensing system of claim 8, wherein said plurality of cavities of each micro pump and the diaphragm situated within each cavity are electrically connected to a controller for electrostatically moving the diaphragm in each cavity to provide a pumping action for moving a fluid within each cavity.

12. The sensing system of claim 11, wherein the controller may provide signals for moving the fluid in one of two possible directions in each micro pump.

13. A sensor system comprising:
   an array of integrated micro pumps for the sampling and detection of airborne chemical and biological species; and
   wherein each micro pump comprises:
      a first layer, at least a portion of which is electrically chargeable;
      a second layer opposing said first layer, at least a portion of which is electrically chargeable;
      said first and second layers forming a cavity therebetween;
      an electrostatically moveable diaphragm disposed between said first and second layers and disposed through said cavity for pumping fluid through said cavity;
      a flow channel formed into at least one of said first and second layers and in fluid communication with said cavity;
      a micro sensor disposed in fluid communication with said flow channel, such that the pumped fluid passes said sensor when pumped into or out of said cavity; and
      at least another layer disposed opposing said second layer and having at least another cavity disposed between said second layer and said at least another layer, and at least another diaphragm disposed between said second layer and said at least another layer, said at least another cavity being in fluid communication with said first cavity; and
      wherein the micro pump has no valve mechanism to assure only one direction of fluid flow in said flow channel.

14. The sensor system of claim 13 wherein said first and second layers, diaphragm, said at least another layer disposed opposing said second layer and said at least another diaphragm disposed between said second layer and said at least another layer are formed from a polymer material.

15. The sensor system of claim 14, wherein selected micro pumps have a first micro sensor type and selected other micro pumps have a second micro sensor type, wherein the first micro sensor type has different sensing characteristics than the second micro sensor type.

16. The sensor system of claim 15, wherein selected micro pumps have a heater means for directly or indirectly heating micro sensors for desorbing an analyte.

17. The sensor system of claim 13, wherein each micro sensor may be one of a group comprising a chemoresistive sensor, a chemo-optical sensor, and a chemo-fluorescent sensor.

* * * * *